US012668580B2

(12) United States Patent
Ren et al.

(10) Patent No.: US 12,668,580 B2
(45) **Date of Patent: *Jun. 30, 2026**

(54) METHOD FOR PREPARING ELECTRONIC-GRADE ETHYLENE SULFATE

(71) Applicant: Wuhan Oxiran Special Chemicals Company, Wuhan (CN)

(72) Inventors: Fan Ren, Wuhan (CN); Liang Wang, Wuhan (CN); Wenchao Song, Wuhan (CN); Rongming Dai, Wuhan (CN); Lichun Liang, Wuhan (CN); Xianmiao Cui, Wuhan (CN)

(73) Assignee: Wuhan Oxiran Special Chemicals Company, Wuhan (CN)

( * ) Notice: Subject to any disclaimer, the term of this patent is extended or adjusted under 35 U.S.C. 154(b) by 429 days.

This patent is subject to a terminal disclaimer.

(21) Appl. No.: 18/353,903

(22) Filed: Jul. 18, 2023

(65) Prior Publication Data

US 2024/0182438 A1 Jun. 6, 2024

(30) Foreign Application Priority Data

Nov. 23, 2022 (CN) ......................... 202211477151.7

(51) Int. Cl.
*C07D 327/10* (2006.01)
*B01F 33/30* (2022.01)
*B01F 101/00* (2022.01)

(52) U.S. Cl.
CPC ............ *C07D 327/10* (2013.01); *B01F 33/30* (2022.01); *B01F 2101/2204* (2022.01)

(58) Field of Classification Search
CPC .................................................... C07D 327/10
See application file for complete search history.

(56) References Cited

U.S. PATENT DOCUMENTS

| | | | | |
|---|---|---|---|---|
| 5,502,153 | A | 3/1996 | Sakashita et al. | |
| 8,926,733 | B2 | 1/2015 | Zheng et al. | |
| 2024/0174628 | A1 * | 5/2024 | Ren | B01J 19/245 |
| 2024/0182439 | A1 * | 6/2024 | Ren | B01F 33/30 |

FOREIGN PATENT DOCUMENTS

| | | | |
|---|---|---|---|
| CN | 115745951 | A | 3/2023 |
| CN | 115894433 | A | 4/2023 |

* cited by examiner

*Primary Examiner* — Laura L Stockton

(57) ABSTRACT

In a method for preparing electronic-grade vinyl sulfate, a sulfur trioxide solution is prepared by dissolving sulfur trioxide with a solution A, an ethylene oxide solution is prepared by mixing a solution B with ethylene oxide, the sulfur trioxide solution and the ethylene oxide solution are pre-cooled, and introduced into a set of microchannel reactors for a real-time reaction to obtain a mixed solution containing crude vinyl sulfate, and then a post-treatment process is carried out to obtain crude vinyl sulfate. With the process, the reaction selectivity is good, and a microchannel reaction can accurately control the reaction energy level due to its rapid mixing and timely heat transfer, which greatly reduces the safety risk and effectively avoids the occurrence of side reactions. One-step synthesis is realized, the atomic economic benefits are significantly improved, and thus the process is a typical low-carbon green chemical reaction.

10 Claims, 6 Drawing Sheets

METHOD FOR PREPARING ELECTRONIC-GRADE ETHYLENE SULFATE

CROSS-REFERENCE TO RELATED APPLICATIONS

This application claims priority to Chinese Patent Application No. 202211477151.7 with a filing date of Nov. 23, 2022. The content of the aforementioned application, including any intervening amendments thereto, is incorporated herein by reference.

TECHNICAL FIELD

The present disclosure relates to the technical field of compound synthesis, in particular to a method for preparing electronic-grade ethylene sulfate.

BACKGROUND

At present, there are many synthetic methods of ethylene sulfate (DTD), including acylation, substitution, addition, dioxane synthesis, oxidation, etc. Various reaction processes have advantages and disadvantages. For example, the acylation process has the advantage that a starting material is cheap and readily available, and the disadvantage that the reaction yield is low, and the starting material sulfuryl chloride or sulfuryl fluoride is a hazardous chemical and is highly corrosive.

The oxidation process is a primary synthesis method for electrolyte additive enterprises at present, a starting material is ethylene glycol, and reacts with dichlorosulfoxide to produce an intermediate vinyl sulfite, and vinyl sulfite is oxidized to form DTD. There are five main schemes for the oxidation process, wherein it is a commonly used method to obtain ethylene sulfate under the catalysis of a ruthenium trichloride aqueous solution by using sodium hypochlorite as an oxidant (scheme 1) at present.

Scheme 1

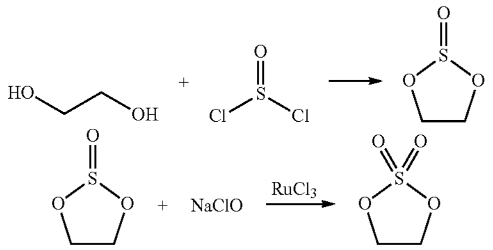

Due to the shorter development time of DTD, the process is not yet mature. In terms of cost, a noble metal catalyst ruthenium trichloride used in Scheme 1 is expensive and difficult to recycle; in terms of product indexes, sodium and chloride ion indexes in a product are likely to exceed the standard, affecting the application effect of the product; and in terms of waste, the use of excessive sodium hypochlorite as a strong oxidant produces a large amount of three wastes, resulting in a large amount of saline wastewater, which has a large impact on the environment.

In 1962, DOW published a patent: U.S. Pat. No. 3,045,027A proposed synthesis of DTD by a reaction of sulfur trioxide with ethylene oxide. However, due to the extremely active properties of reaction raw materials, this process has great safety risks in a kettle reaction. Therefore, there is an urgent need to develop a preparation process that is safe and reliable, has high conversion and high purity, and is suitable for large scale industrial production.

SUMMARY OF PRESENT INVENTION

An objective of the present disclosure is to provide a method for preparing electronic-grade ethylene sulfate with good treatment effects.

In one aspect, the present disclosure provides a method for preparing electronic-grade ethylene sulfate, including the following steps of: preparing a sulfur trioxide solution by dissolving sulfur trioxide with a solution A, preparing an ethylene oxide solution by mixing a solution B with ethylene oxide, pre-cooling the sulfur trioxide solution and the ethylene oxide solution, introducing the pre-cooled sulfur trioxide solution and the pre-cooled ethylene oxide solution into a set of microchannel reactors for a real-time reaction, spray drying the resulting reaction solution to obtain crude ethylene sulfate, dissolving the crude ethylene sulfate, and performing filtration, decolorization, filtration, and recrystallization to obtain the ethylene sulfate finished product with a purity of 99.9% or more.

A reaction equation for the process of the present disclosure is as follows:

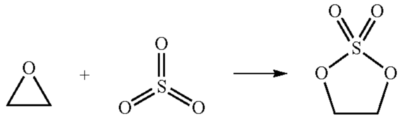

As a preference for the above technical solution, the method for preparing electronic-grade ethylene sulfate provided by the present disclosure further includes some or all of the following technical features:

As an improvement of the above technical solution, a mass ratio of sulfur trioxide to ethylene oxide is 1:(0.5-1.5); the solution A is one or a mixture of more selected from a group consisting of dichloromethane, dichloroethane, trichloromethane, and carbon tetrachloride, and a solvent in the sulfur trioxide solution is 10 mass %-60 mass % of the solution; the solution B is one or a mixture of two selected from a group consisting of trichloromethane and carbon tetrachloride; and a solvent in the ethylene oxide solution is 0~80 mass % of the solution.

As an improvement of the above technical solution, the set of the microchannel reactors consists of at least n microchannel reactors in series, wherein n=3~15.

As an improvement of the above technical solution, the reaction time in each microchannel reactor of the set of the microchannel reactors is 5~20 s, and the reaction pressure is 200~1000 Kpa; the sulfur trioxide solution and the ethylene oxide solution are cooled to −20° C. to 20° C. after a pre-cooling process; and a mixer is selected from a tubular in-line mixer or a microchannel in-line mixer, the in-line mixer is preferably a static mixer, and the pre-cooling temperature after mixing is controlled to be −20° C. to 40° C.

As an improvement of the above technical solution, a mixer is used for a mixing process during preparing the sulfur trioxide solution by dissolving sulfur trioxide with the solution A, and preparing the ethylene oxide solution by mixing the solution B with ethylene oxide.

As an improvement of the above technical solution, a reaction module of the microchannel reactors is made of silicon carbide, glass, stainless steel or ceramic, and a diaphragm pump is used for continuous feeding.

As an improvement of the above technical solution, a catalyst is added while preparing the sulfur trioxide solution by dissolving sulfur trioxide with the solution A, the catalyst is at least one selected from a group consisting of anhydrous pyridine, trimethylamine, triethylamine and N,N-dimethylamide, and an amount of the catalyst added is 0.3%~3%.

As an improvement of the above technical solution, the solution A is used for dissolution during the dissolution and filtration; activated carbon is used for decolorization, and an amount of the activated carbon used is 1%; and after decolorization, filtration is performed, a filtrate is cooled with a saturated solution, filtration is then performed again, and recrystallization is performed.

As an improvement of the above technical solution, a solution E is selected from one or a mixture of more of ethyl acetate, ethyl formate, methyl acetate, and dimethyl carbonate.

As an improvement of the above technical solution, the recrystallization process is repeated at least twice.

Compared with the prior art, the technical solution of the present disclosure has the following beneficial effects:

(1) The reaction selectivity is good, the microchannel conversion is more than 90%, and the gas chromatographic purity is more than 99.9% (with a catalyst), the moisture content is less than 30 ppm, and an acid number is less than 50 ppm.

(2) A microchannel reaction can accurately control the reaction energy level due to its rapid mixing and timely heat transfer, which greatly reduces the safety risk and effectively avoids the occurrence of side reactions.

(3) The reaction steps are simplified to achieve one-step synthesis, the atomic economic benefits are significantly improved, and thus the process is a typical low-carbon green chemical reaction.

(4) The reaction time is significantly reduced from 5 hours in the traditional process to 5 s minimally, and the production efficiency is greatly improved.

The above description is only the summary of the technical solution of the present disclosure, and can be implemented according to the contents of the specification in order to more clearly understand the technical means of the present disclosure, and in order to make the above and other purposes, features and advantages of the present disclosure more obvious and easy to understand, a detailed description is as follows in connection with the preferred embodiments.

BRIEF DESCRIPTION OF THE DRAWINGS

In order to more clearly illustrate the technical solutions of the embodiments of the present disclosure, the drawings of the embodiments are briefly described below.

DETAILED DESCRIPTION OF THE EMBODIMENTS

Specific implementations of the present disclosure are described in detail below, which, as a part of this specification, illustrate the principle of the present disclosure by the embodiments, and other aspects, features and advantages of the present disclosure will become apparent from this detailed description.

Embodiment 1

200 Kg of a 30 wt % sulfur trioxide solution was prepared by dissolving sulfur trioxide with a solvent A, 60 Kg of a 60% ethylene oxide solution was prepared by mixing a solvent B with ethylene oxide, the sulfur trioxide solution, the ethylene oxide solution, and a N,N-dimethylamide solution were pre-cooled to 20° C., and introduced into microchannel reactors while maintaining a mass flow rate of the sulfur trioxide solution at 20 Kg/min, a mass flow rate of the ethylene oxide solution at 6 Kg/min, and a mass flow rate of the N,N-dimethylamide solution at 0.1 Kg/min for a reaction to obtain an ethylene sulfate solution, wherein the reaction pressure was maintained to be 500 KPa or below, the residence time was controlled to be 12 s, the number of reaction modules was 8, and the reaction temperature was controlled to be 20° C.

The resulting crude ethylene sulfate was concentrated to remove the solvents, the crude product was prepared into a 35% ethyl acetate solution, 1% activated carbon was added, the temperature is configured to be about 25° C., decolorization and filtration were performed, the resulting filtrate was cooled to −20° C., recrystallization was performed, and the recrystallized material was spin-dried by a centrifuge, and the spin-dried material was subjected to low-temperature drying under −100 KPa.

The electronic-grade finished product was tested: 66.3 Kg, a calculated yield of about 71.3%, a product purity of 99.644%, the moisture content of 20 ppm, and an acid number of 25 ppm.

Figure 1:
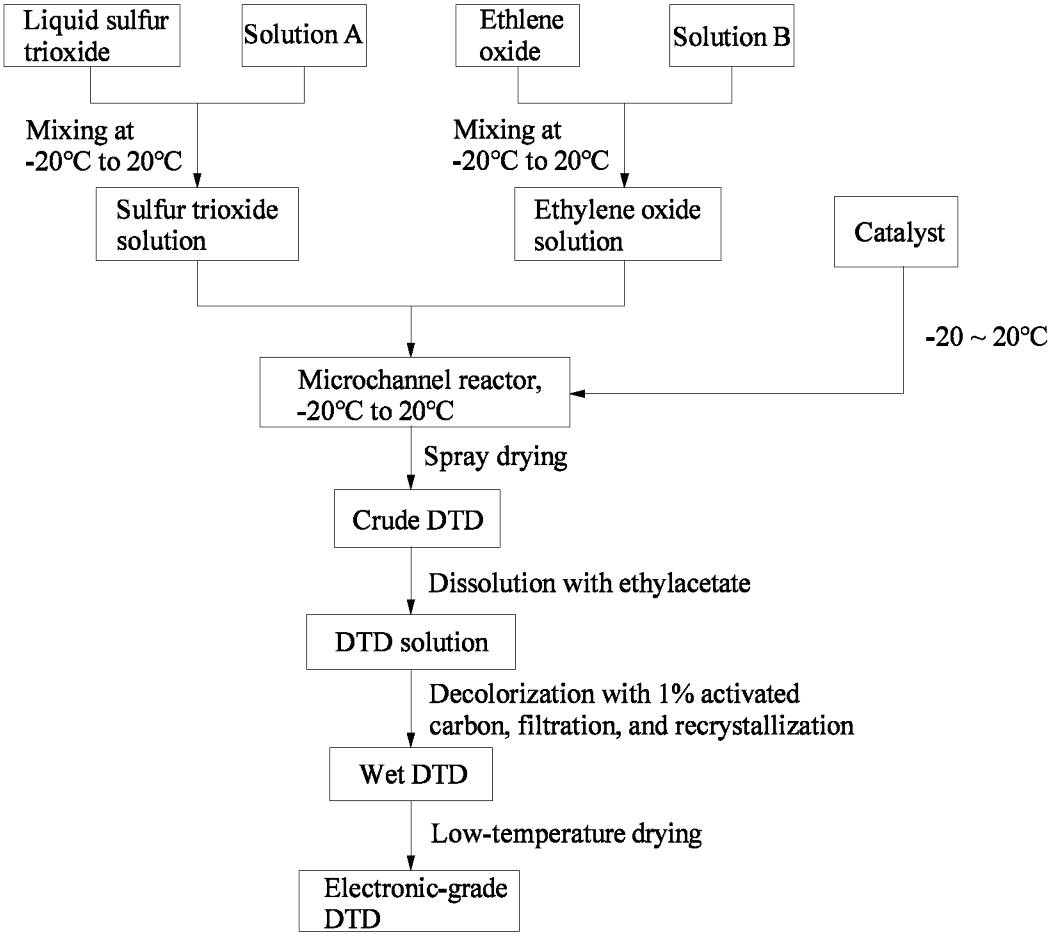
FIG. 1 is a diagram showing a process for preparing electronic-grade ethylene sulfate according to the present disclosure.
Figure 2:
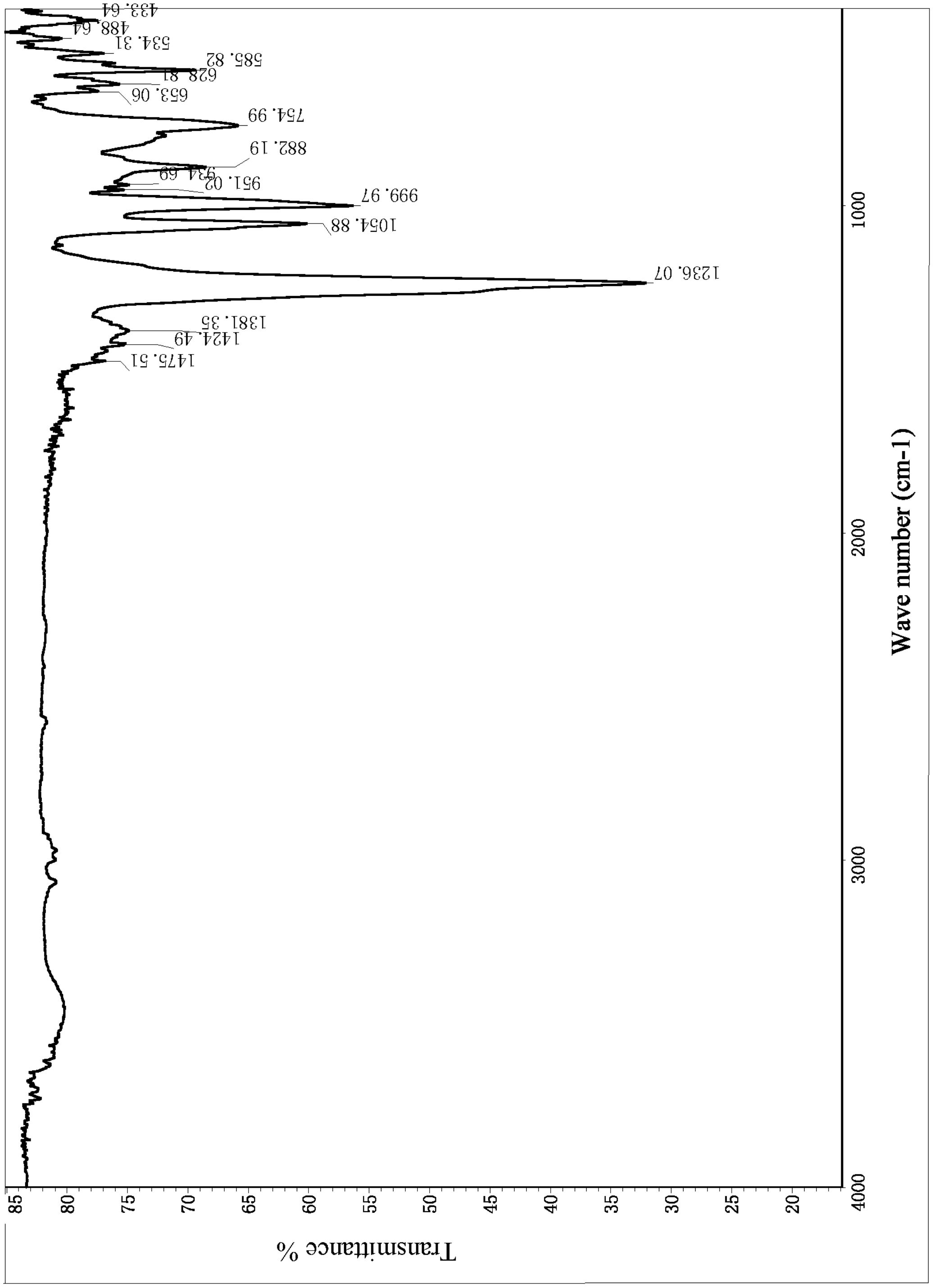
FIG. 2 is an infrared spectrum of a product in Embodiment 1 of the present disclosure.

FIG. 2 is an infrared spectrum of a product in this embodiment. From the figure, it can be seen that its infrared spectrum shows characteristic absorption peaks at 1236 $cm^{-1}$, 1055 $cm^{-1}$, 1000 $cm^{-1}$, 882 $cm^{-1}$, 755 $cm^{-1}$ and 586 $cm^{-1}$. The $CH{=}CH_2$ stretching vibration peak is very weak, indicating that the product purity is high.

Figure 3:
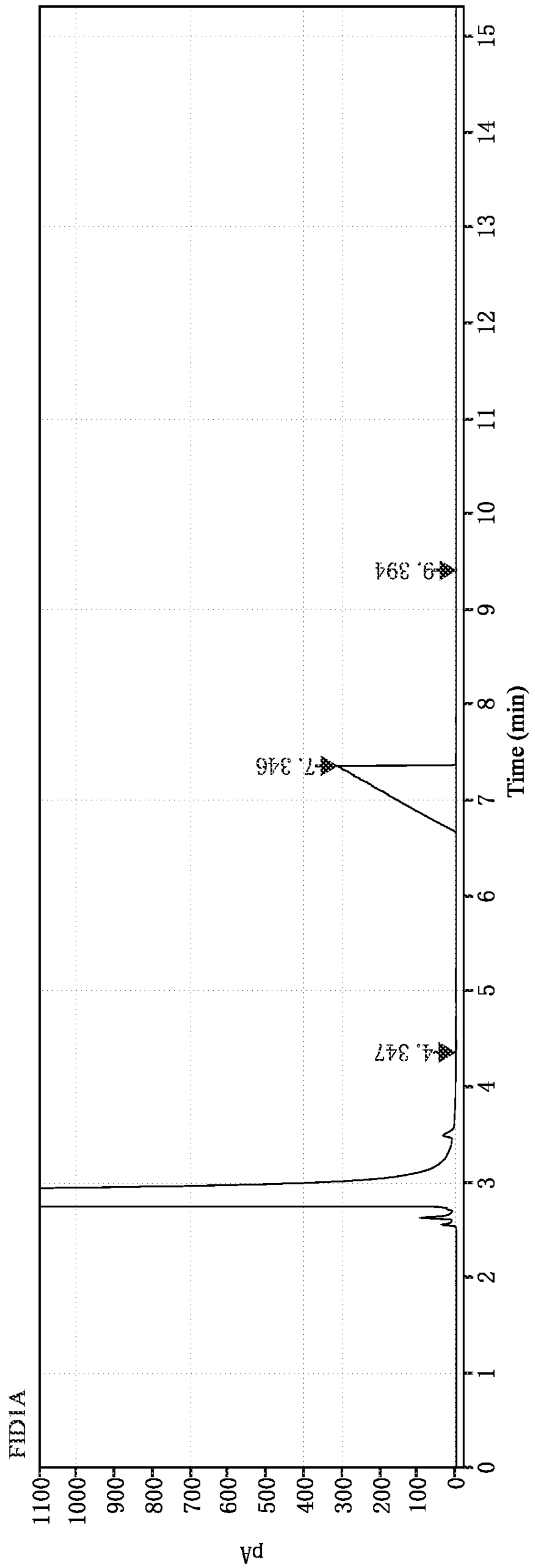
FIG. 3 is a gas chromatogram of the product in Embodiment 1 of the present disclosure.

The product was subjected to gas chromatography, and the results are shown in Table 1, and FIG. 3 is a gas chromatogram of this gas chromatography.

TABLE 1

Gas chromatography data table of the product in Embodiment 1
Signal: FID1A

| Retention time (min) | Type | Peak width (min) | Peak area | Peak height | Peak area % |
|---|---|---|---|---|---|
| 4.347 | MM m | 0.20 | 20.01 | 2.22 | 0.297 |
| 7.346 | VV | 0.80 | 6716.45 | 313.07 | 99.644 |
| 9.394 | MM m | 0.04 | 4.00 | 1.80 | 0.059 |
| | | Sum | 6740.45 | | |

Embodiment 2

200 Kg of a 30 wt % sulfur trioxide solution was prepared by dissolving sulfur trioxide with a solvent A, 60 Kg of a 60% ethylene oxide solution was prepared by mixing a solvent B with ethylene oxide, the sulfur trioxide solution, the ethylene oxide solution, and a N,N-dimethylamide solution were pre-cooled to 20° C., and introduced into micro-channel reactors while maintaining a mass flow rate of the sulfur trioxide solution at 20 Kg/min, a mass flow rate of the ethylene oxide solution at 6 Kg/min, and a mass flow rate of the N,N-dimethylamide solution at 0.1 Kg/min for a reaction to obtain the ethylene sulfate solution. The reaction pressure was maintained to be 500 KPa or below, the residence time was controlled to be 12 s, the number of reaction modules was 8, and the reaction temperature was controlled to be 20° C.

The resulting crude ethylene sulfate was concentrated to remove the solvents, the crude product was prepared into a 32% methyl acetate solution, 1% activated carbon was added, the temperature is configured to be about 25° C., decolorization and filtration were performed, the resulting filtrate was cooled to −20° C., recrystallization was performed, and the recrystallized material was spin-dried by a centrifuge, and the spin-dried material was subjected to low-temperature drying under −100 KPa.

The electronic-grade finished product was tested: 64.6 Kg, a calculated yield of about 69.5%, a product purity of 99.838%, the moisture content of 25 ppm, and an acid number of 30 ppm.

Figure 4:
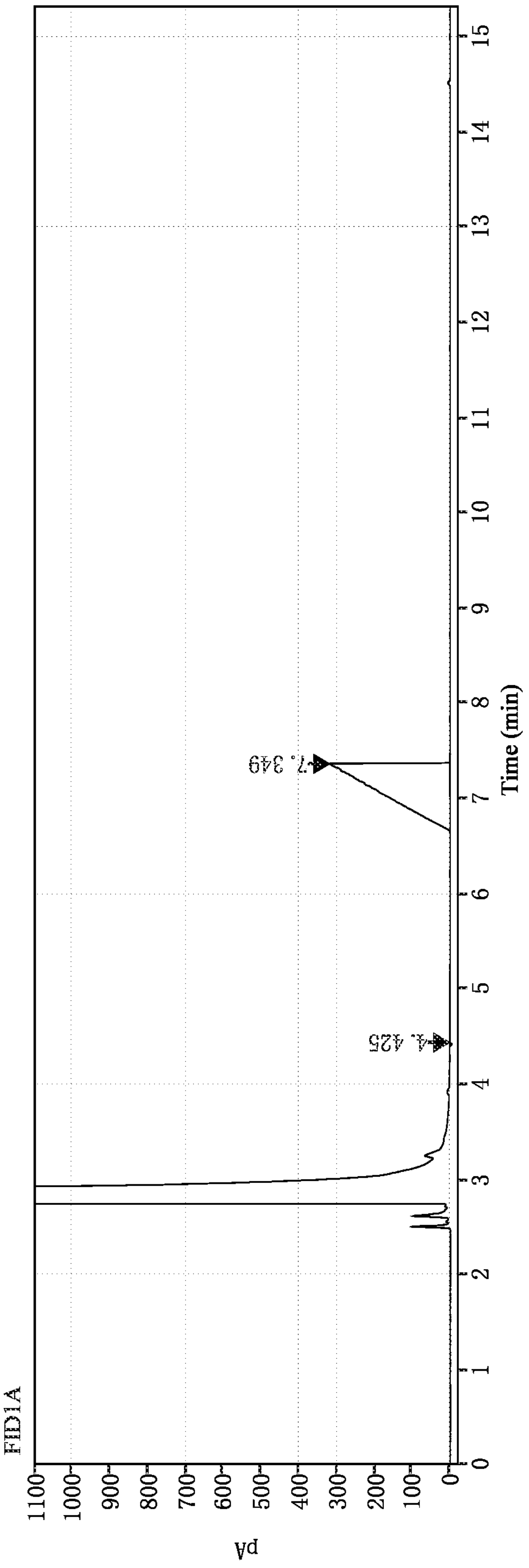
FIG. 4 is a gas chromatogram of a product in Embodiment 2 of the present disclosure.

The product was subjected to gas chromatography, and the results are shown in Table 2, and FIG. 4 is a gas chromatogram of this gas chromatography.

TABLE 2

Gas chromatography data table of the product in Embodiment 2
Signal: FID1A

| Retention time (min) | Type | Peak width (min) | Peak area | Peak height | Peak area % |
|---|---|---|---|---|---|
| 4.425 | MM m | 0.04 | 11.23 | 6.06 | 0.162 |
| 7.349 | BV m | 0.76 | 6918.98 | 318.30 | 99.838 |
| | | Sum | 6930.20 | | |

Embodiment 3

200 Kg of a 30 wt % sulfur trioxide solution was prepared by dissolving sulfur trioxide with a solvent A, 60 Kg of a 60% ethylene oxide solution was prepared by mixing a solvent B with ethylene oxide, the sulfur trioxide solution, the ethylene oxide solution, and a N,N-dimethylamide solution were pre-cooled to 20° C., and introduced into micro-channel reactors while maintaining a mass flow rate of the sulfur trioxide solution at 20 Kg/min, a mass flow rate of the ethylene oxide solution at 6 Kg/min, and a mass flow rate of the N,N-dimethylamide solution at 0.1 Kg/min for a reaction to obtain the ethylene sulfate solution, wherein the reaction pressure was maintained to be 500 KPa or below, the residence time was controlled to be 12 s, the number of reaction modules was 8, and the reaction temperature was controlled to be 20° C.

The resulting crude ethylene sulfate was spray dried to obtain a crude product, the crude product was prepared into a 32% ethyl formate solution, 1% activated carbon was added, the temperature is configured to be about 25° C., decolorization and filtration were performed, the resulting filtrate was cooled to −30° C., recrystallization was performed, and the recrystallized material was spin-dried by a centrifuge, and the spin-dried material was subjected to low-temperature drying under −100 KPa.

The electronic-grade finished product was tested: 67.3 Kg, a calculated yield of about 72.4%, a product purity of 99.960%, the moisture content of 20 ppm, and an acid number of 20 ppm.

Figure 5:
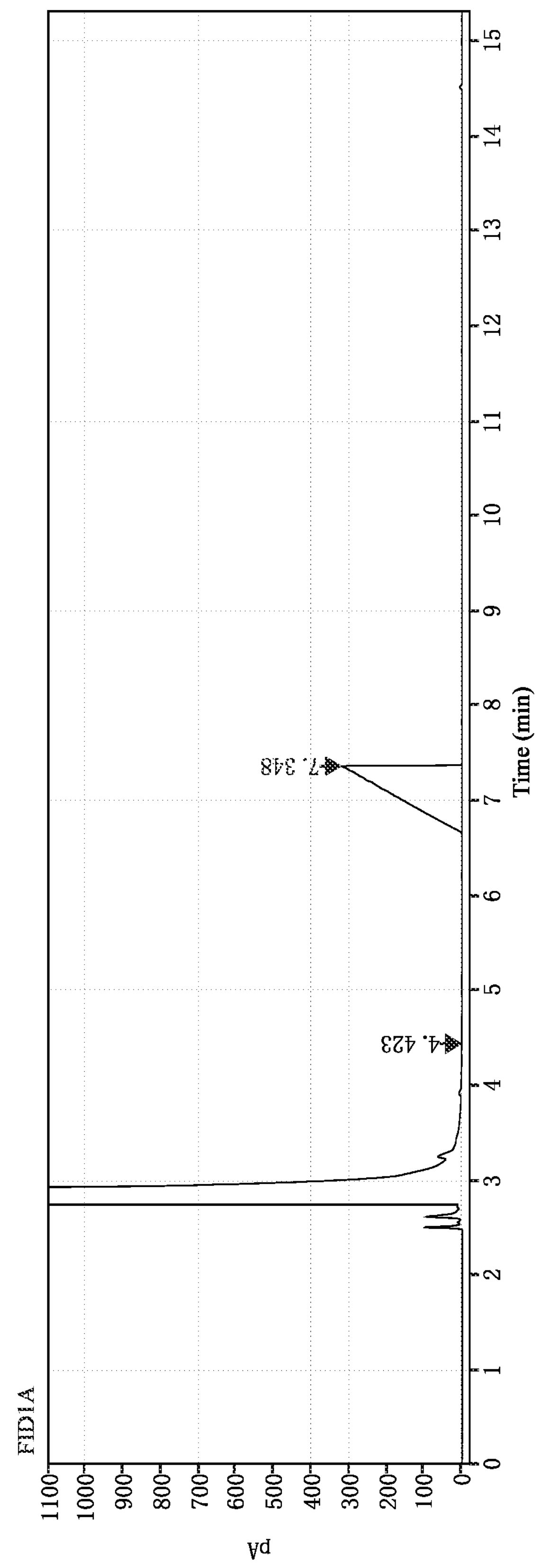
FIG. 5 is a gas chromatogram of a product in Embodiment 3 of the present disclosure.

The product was subjected to gas chromatography, and the results are shown in Table 3, and FIG. 5 is a gas chromatogram of this gas chromatography.

TABLE 3

Gas chromatography data table of the product in Embodiment 3
Signal: FID1A

| Retention time (min) | Type | Peak width (min) | Peak area | Peak height | Peak area % |
|---|---|---|---|---|---|
| 4.423 | MM m | 0.10 | 2.72 | 0.94 | 0.040 |
| 7.348 | BV | 0.80 | 6869.04 | 320.29 | 99.960 |
| | | Sum | 6871.76 | | |

Embodiment 4

200 Kg of a 30 wt % sulfur trioxide solution was prepared by dissolving sulfur trioxide with a solvent A, 60 Kg of a 60% ethylene oxide solution was prepared by mixing a solvent B with ethylene oxide, the sulfur trioxide solution, the ethylene oxide solution, and a N,N-dimethylamide solution were pre-cooled to 20° C., and introduced into micro-channel reactors while maintaining a mass flow rate of the sulfur trioxide solution at 20 Kg/min, a mass flow rate of the ethylene oxide solution at 6 Kg/min, and a mass flow rate of the N,N-dimethylamide solution at 0.1 Kg/min for a reaction to obtain the ethylene sulfate solution. The reaction pressure was maintained to be 500 KPa or below, the residence time was controlled to be 12 s, the number of reaction modules was 8, and the reaction temperature was controlled to be 20° C.

The resulting crude ethylene sulfate was concentrated to remove the solvents, the crude product was prepared into a 32% ethyl acetate solution, 1% activated carbon was added, the temperature is configured to be about 25° C., decolorization and filtration were performed, the resulting filtrate was cooled to −10° C., recrystallization was performed, and the recrystallized material was spin-dried by a centrifuge, and the spin-dried material was subjected to low-temperature drying under −100 KPa.

The electronic-grade finished product was tested: 60.4 Kg, a calculated yield of about 65.1%, a product purity of 99.992%, the moisture content of 15 ppm, and an acid number of 15 ppm.

Figure 6:
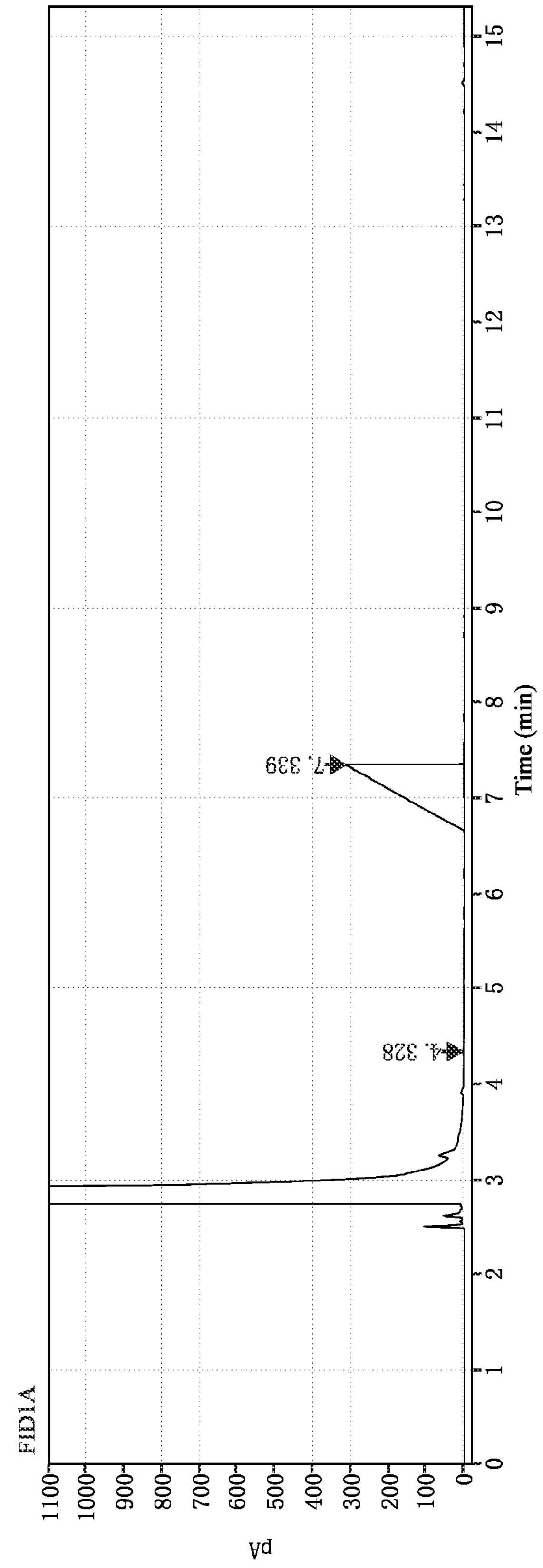
FIG. 6 is a gas chromatogram of a product in Embodiment 4 of the present disclosure.

The product was subjected to gas chromatography, and the results are shown in Table 4, and FIG. 6 is a gas chromatogram of this gas chromatography.

TABLE 4

| Gas chromatography data table of the product in Embodiment 4 Signal: FID1A | | | | | |
|---|---|---|---|---|---|
| Retention time (min) | Type | Peak width (min) | Peak area | Peak height | Peak area % |
| 4.328 | MM m | 0.22 | 0.50 | 0.25 | 0.008 |
| 7.339 | MM m | 0.84 | 6641.18 | 311.05 | 99.992 |
| | | Sum | 6641.68 | | |

The raw materials listed in the present disclosure, the upper and lower limits and interval values of the raw materials in the present disclosure, and the upper and lower limits and interval values of process parameters (such as the temperature, time, etc.) can realize the present disclosure, and the embodiments are not listed here.

The above are only preferred embodiments of the present disclosure, and of course, cannot be intented to limit the scope of the present disclosure. It should be noted that for those of ordinary skill in the art, several improvements and changes can be made without departing from the principle of the present disclosure, and these improvements and changes are also considered to be within the scope of protection of the present disclosure.

What is claimed is:

1. A method for preparing electronic-grade ethylene sulfate, comprising the following steps of:

preparing a sulfur trioxide solution by dissolving sulfur trioxide with a solution A, preparing an ethylene oxide solution by mixing a solution B with ethylene oxide, pre-cooling the sulfur trioxide solution and the ethylene oxide solution, introducing the pre-cooled sulfur trioxide solution and the pre-cooled ethylene oxide solution into a set of microchannel reactors for a real-time reaction, spray drying the resulting reaction solution to obtain crude ethylene sulfate, and dissolving the crude ethylene sulfate, and performing filtration, decolorization, filtration, and recrystallization to obtain the ethylene sulfate finished product with a purity of 99.9% or more.

2. The method according to claim 1, wherein a mass ratio of sulfur trioxide to ethylene oxide is 1:(0.5-1.5); the solution A is one or a mixture of more selected from a group consisting of dichloromethane, dichloroethane, trichloromethane, and carbon tetrachloride, and a solvent in the sulfur trioxide solution is 10 mass %~60 mass % of the solution; the solution B is one or a mixture of two selected from a group consisting of trichloromethane and carbon tetrachloride; and a solvent in the ethylene oxide solution is 0~80 mass % of the solution.

3. The method according to claim 1, wherein the set of the microchannel reactors consists of at least n microchannel reactors in series, and n=3~15.

4. The method according to claim 1, wherein a reaction time in each microchannel reactor of the set of the microchannel reactors is 5~20 s, and a reaction pressure is 200~1000 Kpa; the sulfur trioxide solution and the ethylene oxide solution are cooled to ~20° C. to 20° C. after the pre-cooling process; and a mixer is selected from a tubular in-line mixer or a microchannel in-line mixer, the in-line mixer is a static mixer, and a pre-cooling temperature after mixing is controlled to be −20° C. to 40° C.

5. The method according to claim 1, wherein a mixer is used for a mixing process during preparing the sulfur trioxide solution by dissolving sulfur trioxide with the solution A, and preparing the ethylene oxide solution by mixing the solution B with ethylene oxide.

6. The method according to claim 1, wherein a reaction module of the microchannel reactors is made of silicon carbide, glass, stainless steel or ceramic, and a diaphragm pump is used for continuous feeding.

7. The method according to claim 1, wherein a catalyst is added while preparing the sulfur trioxide solution by dissolving sulfur trioxide with the solution A, the catalyst is at least one selected from a group consisting of anhydrous pyridine, trimethylamine, triethylamine and N,N-dimethylamide, and an amount of the catalyst added is 0.3%~3%.

8. The method according to claim 1, wherein a solution E is used for dissolution during the dissolution and filtration; activated carbon is used for decolorization, and an amount of the activated carbon used is 1%; and after decolorization, filtration is performed, a filtrate is cooled with a saturated solution, filtration is then performed again, and recrystallization is performed.

9. The method according to claim 8, wherein the solution E is one or a mixture of more selected from a group consisting of ethyl acetate, ethyl formate, methyl acetate, and dimethyl carbonate.

10. The method according to claim 1, wherein the recrystallization process is repeated at least twice.

* * * * *